US00PP32128P2

(12) United States Plant Patent
Christensen

(10) Patent No.: US PP32,128 P2
(45) Date of Patent: Aug. 25, 2020

(54) ***PEPEROMIA* PLANT NAMED 'COSTA RICA'**

(50) Latin Name: *Peperomia argyreia*
Varietal Denomination: Costa Rica

(71) Applicant: Per Christensen, Odense S (DK)

(72) Inventor: Per Christensen, Odense S (DK)

(73) Assignee: Gartneriet Tingdal Aps, Odense S (DK)

( * ) Notice: Subject to any disclaimer, the term of this patent is extended or adjusted under 35 U.S.C. 154(b) by 0 days.

(21) Appl. No.: 16/602,707

(22) Filed: Nov. 22, 2019

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new cultivar of *Peperomia* plant named 'Costa Rica' that is characterized by heart shaped leaves that are grey-green with green areas surrounding the veins on the upper surface and yellow-green on the lower surface.

1 Drawing Sheet

Botanical classification: *Peperomia argyreia.*
Variety denomination: 'Costa Rica'.

BACKGROUND OF THE INVENTION

The present invention relates to a new and distinct cultivar of *Peperomia* plant botanically known as *Peperomia argyreia* and hereinafter referred to by the cultivar name 'Costa Rica'.

'Costa Rica' was discovered as a naturally occurring leaf mutation of an unnamed *Peperomia argyreia* plant in May of 2014. The new cultivar was discovered in a population of *Peperomia argyreia* plants in a controlled environment and cultivated area of Odense, Denmark.

Asexual reproduction of the new cultivar 'Costa Rica' first occurred by leaf cuttings in May of 2015 in Odense, Denmark. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Costa Rica'. These traits in combination distinguish 'Costa Rica' as a new and distinct cultivar apart from other existing varieties of *Peperomia* known by the inventor.

1. *Peperomia* 'Costa Rica' exhibits heart shaped leaves.
2. *Peperomia* 'Costa Rica' exhibits leaves that are grey-green with green areas surrounding the veins on the upper surface and yellow-green on the lower surface.

The closest comparison cultivars are *Peperomia* 'Sunrise' (U.S. Plant Pat. No. 29,417) and *Peperomia* 'Watermelon' (not patented). 'Costa Rica' is distinguishable from 'Sunrise' by the following characteristics:

1. *Peperomia* 'Costa Rica' exhibits heart shaped leaves. In comparison, the leaves of 'Sunrise' are oval shaped with a more pointed tip.
2. *Peperomia* 'Costa Rica' exhibits larger leaves than the leaves of 'Sunrise'.

3. *Peperomia* 'Costa Rica' exhibits a fewer number of leaves than the number of leaves of 'Sunrise'.
4. *Peperomia* 'Costa Rica' exhibits leaves that are grey-green with green areas surrounding the veins on the upper surface and yellow-green on the lower surface. In comparison, the leaves of 'Sunrise' are grey-green with dark green veins on the upper surface and pink-red leaves on the lower surface.

'Costa Rica' is distinguishable from 'Watermelon' by the following characteristics:

1. *Peperomia* 'Costa Rica' exhibits heart shaped leaves. In comparison, the leaves of 'Watermelon' are teardrop shaped.
2. *Peperomia* 'Costa Rica' exhibits smaller leaves than the leaves of 'Watermelon'.
3. *Peperomia* 'Costa Rica' exhibits leaves that are grey-green with green areas surrounding the veins on the upper surface and yellow-green on the lower surface. In comparison, the leaves of 'Watermelon' are green with silver-grey patches.

'Costa Rica' is distinguishable from the parent plant by the following characteristics:

1. *Peperomia* 'Costa Rica' exhibits heart shaped leaves. In comparison, the leaves of the parent plant are teardrop shaped.
2. *Peperomia* 'Costa Rica' exhibits smaller leaves than the leaves of the parent plant.

BRIEF DESCRIPTION OF THE DRAWING

The accompanying photograph illustrates the distinguishing traits of *Peperomia* 'Costa Rica'. The photograph shows an overall view of a 30 week old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Peperomia* cultivar named 'Costa Rica'. Data was collected in Odense, Denmark from 30 week old plants grown in a glass greenhouse in 14.0 cm. diameter containers. The time of year was Autumn and the temperature range was 20-23 degrees Centigrade during the day and 18-20 degrees Centigrade at night. The light level was natural light level. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'Costa Rica' has not been tested under all possible conditions and phenotypic differences may be observed with variations in environmental, climatic, and cultural conditions, however, without any variance in genotype.

Botanical classification: *Peperomia argyreia* 'Costa Rica'.

Annual or perennial: Perennial.

Parentage: 'Costa Rica' is a naturally occurring leaf mutation of an unnamed *Peperomia argyreia* plant.

Plant type: Potted plant.

Growth habit: Rosette of leaves forming very short thick stems.

Plant shape: Globe shaped with inflorescences above the foliage.

Suitable container size: 10.5 cm. pots or larger.

Plant height to top of foliage: Average 18.0 cm.

Plant height to top of floral plane: Average 25.9 cm.

Plant width: Average 30.1 cm.

Vigor: Moderate.

Growth rate: Moderate.

Low temperature tolerance: 10° Centigrade.

High temperature tolerance: 35° Centigrade.

Propagation: Leaf cuttings.

Time to initiate roots (summer): 28 days at 20° C.

Time to initiate roots (winter): 35 days at 20° C.

Time to produce a rooted cutting (summer): 80 days at 20° C.

Time to produce a rooted cutting (winter): 100 days at 20° C.

Crop time: Approximately 30 weeks in Odense, Denmark.

Root system: Fine and fibrous.

Plant fragrance: None.

Stem:

- *Branching habit*.—Leaves in rosettes forming very short thick stems.
- *Pinching*.—Not required.
- *Number of main stems per plant*.—Average 5.
- *Number of lateral branches per plant*.—Average 4.
- *Lateral branch dimensions*.—Average 1.7 cm. in length and 0.7 cm. in width.
- *Internode length*.—Average 0.15 cm.
- *Stem appearance*.—Succulent.
- *Stem shape*.—Rounded.
- *Stem texture*.—Smooth.
- *Stem luster*.—Moderately glossy.
- *Stem pubescence*.—Absent.
- *Stem angle*.—Average 10 degrees.
- *Stem strength*.—Moderately strong.
- *Stem color* (*young*).—183A.
- *Stem color* (*mature*).—In between 183A and 200B.
- *Internode color*.—In between 183A and 200B.

Foliage:

- *Leaf arrangement*.—Alternate.
- *Compound or single*.—Single.
- *Quantity of leaves per lateral branch*.—Average 7.
- *Leaf shape*.—Cordate, perfoliate.
- *Leaf aspect*.—Moderately concave.
- *Leaf apex*.—Apiculate.
- *Leaf base*.—Hastate, lobes touching against each other perpendicular to leaf plane.
- *Leaf dimensions*.—Average 9.6 cm. in length and 9.0 cm. in width.
- *Texture upper surface*.—Glabrous, moderately leathery, slightly velvety.
- *Texture lower surface*.—Glabrous, moderately leathery.
- *Leaf luster upper surface*.—Moderately glossy.
- *Leaf luster lower surface*.—Slightly glossy.
- *Pubescence*.—Absent (both surfaces).
- *Leaf margin*.—Entire.
- *Leaf lobed*.—Not lobed.
- *Leaf rugose*.—Not rugose (both surfaces).
- *Venation pattern*.—Parallel, slightly furrowed.
- *Young leaf color* (*upper surface*).—N191C.
- *Young leaf color* (*lower surface*).—147D.
- *Mature leaf color* (*upper surface*).—191A, area around veins between 137A and 143A.
- *Mature leaf color* (*lower surface*).—148D.
- *Vein color* (*upper surface*).—144A and 144B.
- *Vein color* (*lower surface*).—146B to 146C, at petiole 183A to 183B.

Petiole:

- *Petiole dimensions*.—Average 12.2 cm. in length and 0.4 cm. in diameter.
- *Petiole texture*.—Glabrous.
- *Petiole luster*.—Moderately glossy on both sides.
- *Petiole pubescence*.—Absent.
- *Petiole strength*.—Low.
- *Petiole color* (*both sides*).—183A with fine striped lenticels 147D.

Flower:

- *Inflorescence type*.—Axillary compound spike.
- *Inflorescence dimensions*.—Average 7.5 cm. in length and 0.3 cm. in diameter.
- *Quantity of flowers per inflorescence*.—Average over 1,250 per spike.
- *Quantity of flowers per plant*.—Average over 1,250.
- *Quantity of buds per plant*.—Average over 3,750.
- *Quantity of flowers and buds per plant*.—Average over 5,000.
- *Fragrance*.—None.
- *Bud length*.—Average 0.4 mm.
- *Bud diameter*.—Average 0.4 mm.
- *Bud shape*.—Flattened orbicular.
- *Bud texture*.—Glabrous, moderately velvety.
- *Bud luster*.—Slightly glossy.
- *Bud color*.—146C.
- *Flower type and form*.—Flowers consist of two stamens, one pistil and one bract.
- *Flower aspect*.—Outward.
- *Flower shape*.—Rotate, two stamens, one pistil and one bract, no petals or sepals.
- *Flower dimensions*.—Average 0.8 mm. in height and 0.5 mm. in diameter.
- *Flower longevity*.—Approximately 1 month.
- *Natural flowering season*.—Fall to late spring.
- *Persistent or self-cleaning*.—Self-cleaning.

Bracts:

- *Bract arrangement*.—One flower bract is located below the stamens and pistil and two peduncle bracts are located at the peduncle axils.

*Flower bract dimensions*.—Average 0.4 mm. in length and 0.4 mm. in width.
*Flower bract shape*.—Orbicular.
*Flower bract color*.—147C.
*Peduncle bract dimensions*.—Average 1.3 cm. in length and 0.3 mm. in width.
*Peduncle bract shape*.—Lanceolate.
*Peduncle bract color upper side*.—144A to 144B, fading to 182B towards base.
*Peduncle bract color lower side*.—182B, margins and tip 144A to 144B.

Peduncle:
*Peduncle dimensions*.—Average 24.5 cm. in length and 0.3 cm. in diameter.
*Peduncle angle*.—15 degrees from vertical.
*Peduncle strength*.—Weak.
*Peduncle texture*.—Smooth.
*Peduncle luster*.—Slightly glossy.
*Peduncle color*.—187B with very fine stripes 147D.

Reproductive organs:
*Stamen number*.—2.
*Anther shape*.—Kidney shaped.
*Anther length*.—Average 0.1 mm.
*Anther width*.—Average 0.15 mm.
*Anther color*.—145C.
*Filament length*.—Average 0.1 mm.
*Filament color*.—146C.
*Amount of pollen*.—Low.
*Pollen color*.—157D.
*Number of pistils*.—1.
*Pistil length*.—Average 0.2 mm.
*Stigma shape*.—Flattened, rounded.
*Stigma dimensions*.—0.2 mm. in length and 0.2 mm. in diameter.
*Stigma color*.—146B.
*Style*.—Absent, stigma sessile.
*Ovary color*.—144B.

Fruit and seed: 'Costa Rica' has not produced fruit or seed to date.

Disease and pest resistance: Disease and pest resistance do not differ from other *Peperomia* varieties.

The invention claimed is:

1. A new and distinct variety of *Peperomia* plant named 'Costa Rica' as described and illustrated.

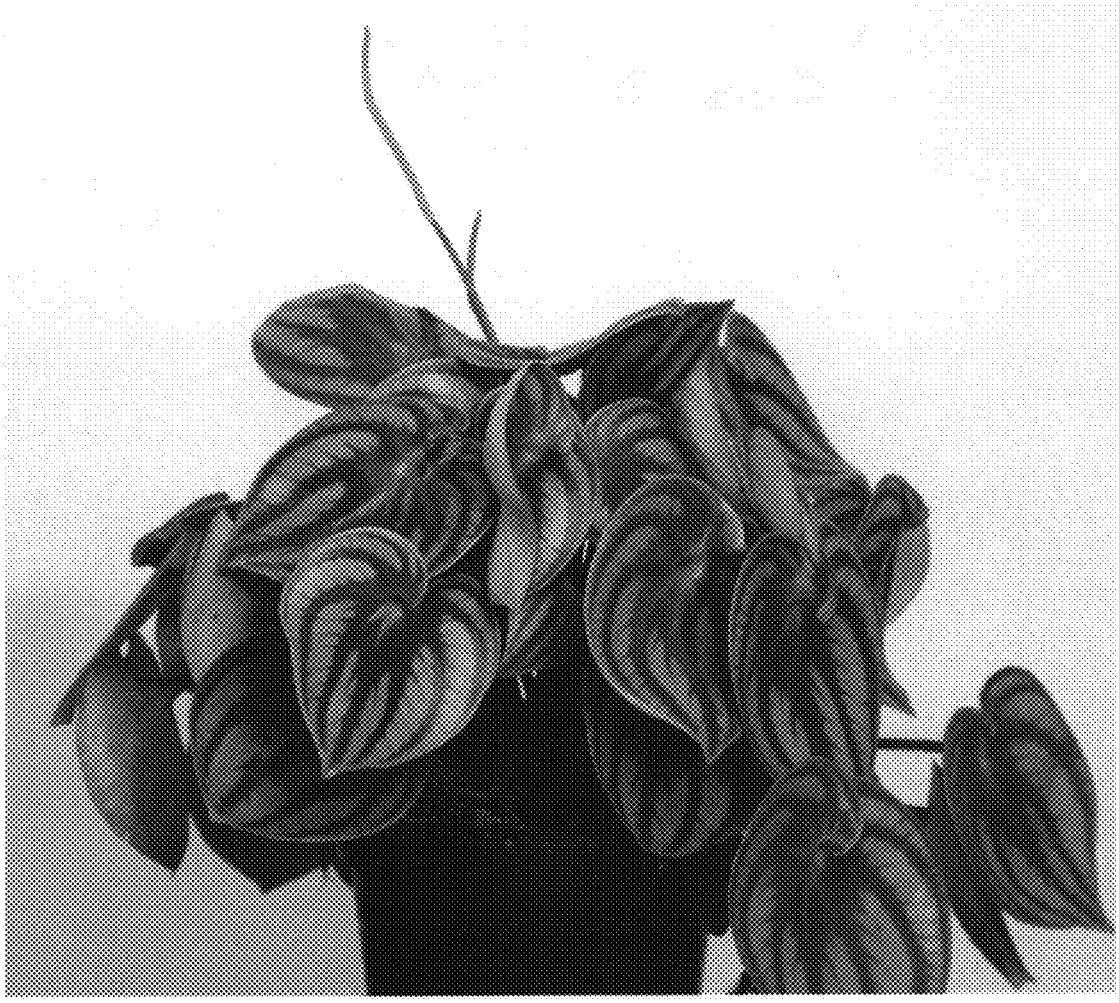

* * * * *